(12) United States Patent
Sholtis

(10) Patent No.: US 7,941,324 B1
(45) Date of Patent: May 10, 2011

(54) METHOD AND SYSTEM FOR IDENTIFICATION OF A PATIENT

(75) Inventor: Steven A. Sholtis, El Dorado Hills, CA (US)

(73) Assignee: Intuit Inc., Mountain View, CA (US)

( * ) Notice: Subject to any disclaimer, the term of this patent is extended or adjusted under 35 U.S.C. 154(b) by 941 days.

(21) Appl. No.: 11/796,703

(22) Filed: Apr. 26, 2007

(51) Int. Cl.
*G06Q 10/00* (2006.01)
*G06Q 50/00* (2006.01)
*A61B 5/00* (2006.01)
*G06F 19/00* (2011.01)

(52) U.S. Cl. .............................................. 705/2; 705/3
(58) Field of Classification Search .................... 705/2–3
See application file for complete search history.

(56) References Cited

U.S. PATENT DOCUMENTS

| | | | | |
|---|---|---|---|---|
| 4,993,068 A * | 2/1991 | Piosenka et al. | ............ | 713/186 |
| 5,930,804 A * | 7/1999 | Yu et al. | ............ | 1/1 |
| 6,587,830 B2 * | 7/2003 | Singer | ............ | 705/3 |
| 7,194,426 B1 | 3/2007 | Box | | |
| 2001/0047281 A1 * | 11/2001 | Keresman et al. | ............ | 705/2 |
| 2003/0217276 A1 * | 11/2003 | LaCous | ............ | 713/186 |
| 2004/0129787 A1 * | 7/2004 | Saito et al. | ............ | 235/492 |
| 2004/0255127 A1 * | 12/2004 | Arnouse | ............ | 713/186 |
| 2007/0005394 A1 | 1/2007 | Bleyendaal et al. | | |
| 2007/0078687 A1 | 4/2007 | Dettinger et al. | | |
| 2007/0197882 A1 | 8/2007 | Smith et al. | | |

OTHER PUBLICATIONS

"The Power Behind Your Records"; Medic Alert Magazine; vol. 3, Issue 2; Apr. 1, 2006; (13 pages).

* cited by examiner

*Primary Examiner* — Gerald J. O'Connor
*Assistant Examiner* — Amber Altschul
(74) *Attorney, Agent, or Firm* — Osha • Liang LLP

(57) ABSTRACT

A method for obtaining healthcare that includes submitting biometric identification data to a Personal Health History (PHH) account that includes a PHH for a patient, permitting a healthcare provider to obtain the biometric identification data, wherein the healthcare provider accesses the PHH account with the biometric identification data to obtain the PHH, and receiving a treatment for a health condition of the patient, wherein the treatment is administered by the healthcare provider accessing the PHH.

32 Claims, 5 Drawing Sheets

METHOD AND SYSTEM FOR IDENTIFICATION OF A PATIENT

CROSS-REFERENCE TO RELATED APPLICATIONS

The present application contains subject matter that may be related to the subject matter in the following U.S. patent application, which is assigned to a common assignee: "Method and System for Collaborative Personal Health History" filed on Apr. 26, 2007 with Ser. No. 11/796,627, which is hereby incorporated by reference.

BACKGROUND

When injured or in need medical attention, individuals make visits to appropriate healthcare providers. Individuals may also schedule visits to healthcare providers for routine examinations. For example, an individual may have regular wellness checks with a family practice physician and may be treated by a variety of specialists as health conditions arise. Further, the individual may make one or more visits to an emergency room when accidents occur.

Typically, upon an initial visit to a healthcare provider, the individual or a guardian for the individual is given a paper-based form to enter the individual's personal health history. The personal health history typically includes data such as types and dates of surgeries, names and types of illnesses, medications, medical history of parents and grandparents, etc. After submitting the data in the form, the healthcare provider creates a medical record for the individual.

In subsequent visits to the healthcare provider, the staff of the healthcare provider may request individuals to identify themselves, such as by providing a name or a driver's license. Using the identification, the staff finds a physical file containing the medical record and gives the file to the healthcare provider. Using the file, the healthcare provider treats the individual.

During the initial visit and subsequent visits, the healthcare provider updates the medical record to include information about the visit. Thus, the healthcare provider's medical record for the patient contains the personal health history entered on the form as well as a history of the patient's interaction with the healthcare provider.

SUMMARY

In general, in one aspect, the invention relates to a method for obtaining healthcare that includes submitting biometric identification data to a Personal Health History (PHH) account that includes a PHH for a patient, permitting a healthcare provider to obtain the biometric identification data, wherein the healthcare provider accesses the PHH account with the biometric identification data to obtain the PHH, and receiving a treatment for a health condition of the patient, wherein the treatment is administered by the healthcare provider accessing the PHH.

In general, in one aspect, the invention relates to a method for patient identification that includes receiving an identification request from a healthcare provider, wherein the identification request comprises biometric identification data for a patient, accessing a PHH account of the patient using the biometric identification data received from the healthcare provider, obtaining a common identifier for the patient from the PHH account, and sending the common identifier to the healthcare provider.

In general, in one aspect, the invention relates to a system for patient identification that includes a PHH repository for storing a PHH account associated with a patient, and a PHH interface configured to receive an identification request from a healthcare provider, wherein the identification request comprises biometric identification data obtained from a biometric scanner used by the healthcare provider, access the PHH account of the patient using the biometric identification data received from the healthcare provider, obtain a common identifier for the patient from the PHH account, and send the common identifier to the healthcare provider.

In general, in one aspect, the invention relates to a computer readable medium that includes computer readable program code embodied therein for causing a computer system to receive an identification request from a healthcare provider, wherein the identification request comprises biometric identification data for a patient, access a PHH account of the patient using the biometric identification data received from the healthcare provider, obtain a common identifier for the patient from the PHH account, and send the common identifier to the healthcare provider.

In general, in one aspect, the invention relates to a computer readable medium that includes computer readable program code embodied therein for causing a computer system to submit biometric identification data to a Personal Health History (PHH) account that includes a PHH for a patient, obtain the biometric identification data from a patient, wherein a healthcare provider accesses the PHH account with the biometric identification data to obtain the PHH, and receive a treatment for a health condition of the patient, wherein the treatment is administered by the healthcare provider accessing the PHH.

Other aspects of the invention will be apparent from the following description and the appended claims.

DETAILED DESCRIPTION

Figure 1:
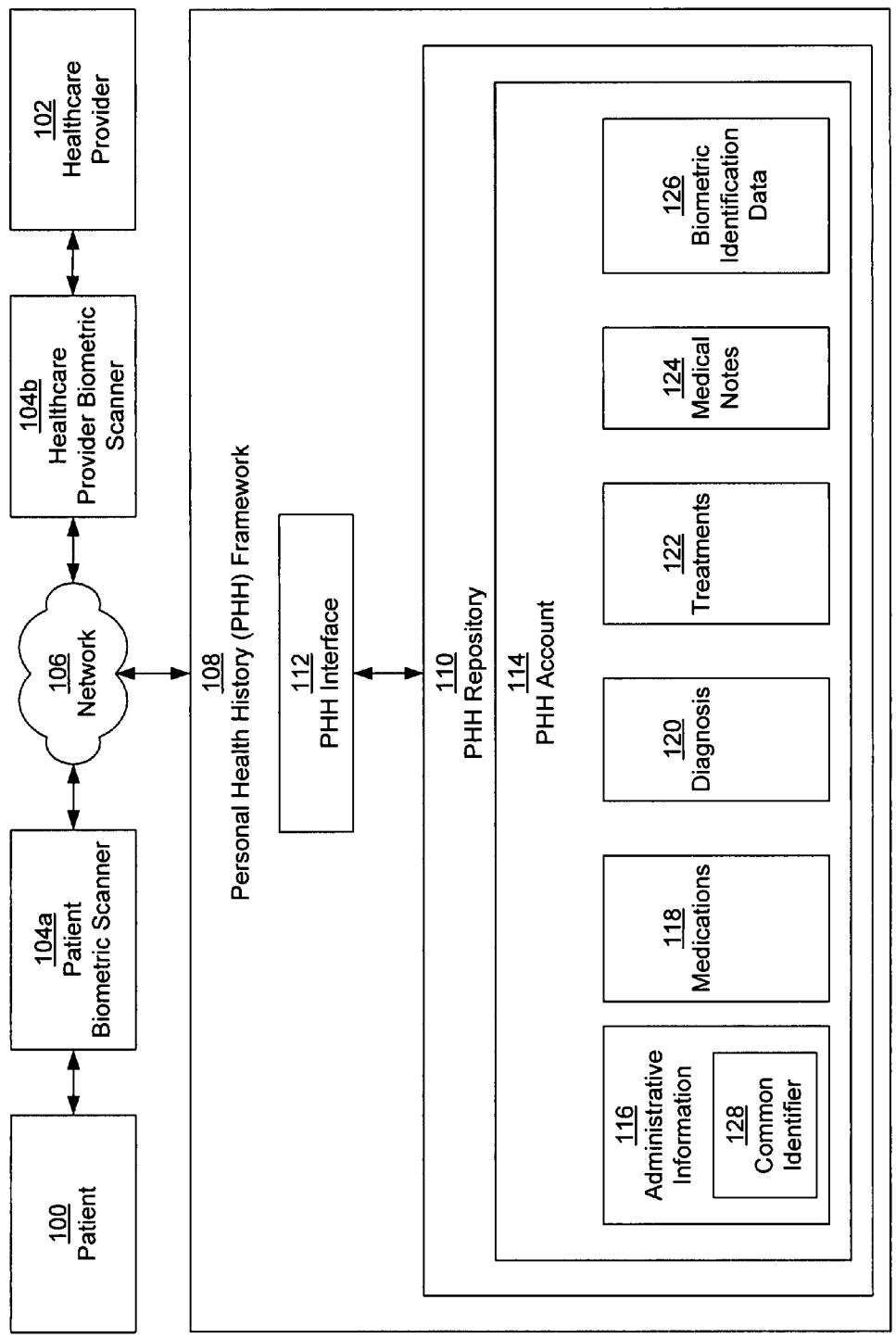
FIG. 1 shows a schematic diagram of a system in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention provide a method and system for identifying a patient using biometric identification data stored in a personal health history (PHH) repository, which is accessible to a healthcare provider and a patient. Thus, a patient may store both the biometric identification data and a common identifier for an online account in the PHH repository. A healthcare provider, who may or may not be known to the patient, may use the biometric identification data from the patient to obtain the common identifier from the PHH repository in order to identify the patient. In one or more embodiments of the invention, a PHH is stored with the biometric identification data, which may be obtained and used by the healthcare provider to treat the patient.

FIG. 1 shows a schematic diagram of a system in accordance with one or more embodiments of the invention. FIG. 1 shows a schematic diagram of a system for collaborative PHH in accordance with one or more embodiments of the invention. As shown in FIG. 1, the system includes a patient (100), a healthcare provider (102), biometric scanners (e.g., patient biometric scanner (104a), healthcare provider biometric scanner (104b)), a network (106), and a PHH framework (108). Each of these components is described below.

A patient (100) is any individual who, at some point, is under the care of a healthcare provider (102) in one or more embodiments of the invention. For example, a patient may be a person who receives a surgery, has an office visit with a healthcare provider, schedules an office visit, fills a prescription, visits an emergency room, or other health-related activities. Further, a patient (100) may also be considered capable of accessing and interacting with the healthcare framework when a guardian (i.e., an individual or entity with authority to act on behalf of the patient) accesses and interacts with the framework on behalf of the patient. One skilled in the art will appreciate that a guardian, as used herein, should be understand as a someone that has been given some authority by the patient (100) and may not possess a medical power of attorney or durable power of attorney for healthcare from the patient (100).

A healthcare provider (102) is any individual or entity that provides a medical or other healthcare service. For example, a healthcare provider (102) may be a physician, nurse, hospital, pharmacist, therapist, dentist, medical assistant, traditional therapy practitioner, lab technician, a clinic, a paramedic, a medical technician, or any other provider of a medical or healthcare service. In one or more embodiments of the invention, if a patient is treated by multiple healthcare providers, then the healthcare providers may or may not be associated with each other. Specifically, the healthcare providers may belong to the same managed care group and network or to different managed care groups and networks. For the purposes of the description, a healthcare provider (102) is considered to interact with the PHH framework when an assistant of the healthcare provider interacts with the PHH framework on behalf of the healthcare provider (102).

Both the patient (100) and the healthcare provider (102) may have a biometric scanner (e.g., patient biometric scanner (104a), healthcare provider biometric scanner (104b)). A biometric scanner (e.g., patient biometric scanner (104a), healthcare provider biometric scanner (104b)) is a device that includes functionality to obtain biometric identification data (126) from a patient (100).

Biometric identification data (126) is data that is based on the biology of a patient (100) and may be used for identifying a patient. For example, biometric identification data (126) may be derived from a biological print (e.g., fingerprint, palm print, toe print, or other such print from the skin), retinal scan, or Deoxyribonucleic acid (DNA) sequence, etc. Alternatively, biometric identification data may be derived from an image of the patient or a portion of the patient. Thus, the biometric scanner (e.g., patient biometric scanner (104a), healthcare provider biometric scanner (104b)) may be a fingerprint scanner, a retina scanner, a device used to identity a DNA sequence from biological matter of a patient, recognition software for interpreting image data, or other identification devices.

The patient biometric scanner (104a) may be used to store biometric identification data in the PHH account (114) (described below). Further, the patient biometric scanner (104a) may be a device used by a patient (100) to access a PHH account. Similarly, the healthcare provider biometric scanner (104b) may be a device used by a healthcare provider (102) to access the PHH account (114) to treat the patient (100). The patient biometric scanner (104a) may be the same biometric scanner as the healthcare provider biometric scanner (104b).

In one or more embodiments of the invention, the patient biometric scanner (104a) and the healthcare provider biometric scanner (104b) are connected, directly or indirectly, via a network (106). The network (106) may be a local area network (LAN), a wide area network (e.g., the Internet), telephone networks, mobile networks, and other communication mediums or any combination thereof. Further, in one or more embodiments of the invention, the patient (100) and the healthcare provider (102) may access a PHH framework (108) via the network (106). One skilled in the art will appreciate that the PHH framework (108) may also accessed either online (i.e., connected to the network) or offline (i.e., away from the network either temporarily or for a period of time). If accessed offline, then the PHH framework (108) include functionality to synchronize information when online access is restored.

A PHH framework (108) includes functionality to maintain and permit access to a patient's PHH. The PHH framework (108) may be maintained on a single computer system, such as a server, or distributed across multiple computer systems. The PHH framework (108) includes a PHH repository (110) and a PHH interface (112) in accordance with one or more embodiments of the invention.

A PHH repository (110) is a storage unit (e.g., a file system, database, directory server, or any other type of storage mechanism for data) for maintaining a patient's PHH in accordance with one or more embodiments of the invention. A patient's PHH is maintained as healthcare data in a PHH account (114) in the PHH repository (110). Specifically, the PHH account (114) for the patient (100) is an organized storage system for maintaining healthcare data that is a part of the PHH of the patient (100).

Moreover, the PHH account (114) may be remotely accessible by the patient (100) and healthcare provider (102) in one or more embodiments of the invention. The healthcare data in the PHH account (114) may include administrative information (116), medications (118), diagnosis (120), treatments (122), medical notes (124), biometric identification data (126), as well as any other type of healthcare data that is a part of the PHH of a patient (100). Each of the aforementioned types of healthcare data is described below.

Administrative information (116) is information about the patient (100) and the PHH account (114) for the patient (100). Administrative information (116) includes a common identifier (128). A common identifier (128) is an identifier which is recognizable by the healthcare provider. For example, a common identifier may be a first and last name, a social security number, a driver's license number, an identification card number, last name and date of birth, as well as other identifiers. In addition to the common identifier (128), administrative information (116) may also include address and contact information, health insurance information, emergency contact information, PHH account preferences, etc.

Medications (118) may include current and past medications that the patient has used as well as both prescription and non-prescription medications. Additionally, medications (118) may specify dosage specifics such as amount and time for administering the medications. Further, medications (118) may be divided into categories, such as necessary medications (e.g., insulin) and unnecessary medications (e.g., vitamins).

Diagnosis (120) is information regarding the current and past conditions affecting the patient (100). For example, a diagnosis may be an illness, affliction, or special capability of the patient (100). A diagnosis (120) may be stored with or separately from corresponding treatments (122). Treatments (122) include any mechanism for preventing or alleviating healthcare-related conditions. For example, treatments may include data related to therapy, medication regimen, surgeries performed, etc.

Further, the PHH account (114) for the patient may also include medical notes (124). Medical notes (124) are additional healthcare data that may be provided by the patient (100) and/or the healthcare provider (102). For example, medical notes (124) may include lab results and interpretation of lab results, blood pressure monitoring information, patient temperature, general wellness information, pain information, etc. Further, medical notes (124) may also include information about the personal health history of family members of the patient (100), such as illnesses afflicting a parent or grandparent of the patient (100). For example, the medical notes may include history of cancer, diabetes, or other conditions which elevate the patient's probability of having the condition when a family member is afflicted with the condition.

Biometric identification data (126) in the PHH account (114) is the biometric identification data obtained from the patient biometric scanner (104a) (discussed above). In one or more embodiments of the invention, the biometric identification data (126) may be used to identify and obtain a patient's PHH in the form of healthcare data from the PHH account (114) for the patient (100). Specifically, the PHH repository (110) may be indexed on the biometric identification data (126) in one or more embodiments of the invention.

Continuing with FIG. 1, the PHH repository (110) is connected to a PHH interface (112) in accordance with one or more embodiments of the invention. A PHH interface (112) includes functionality to interact with the patient (100), the healthcare provider (102), and the PHH repository (110). Specifically, the PHH interface (112) includes functionality to authenticate the user (e.g., patient (100), healthcare provider (102)) and determine whether the user is authorized to access the PHH account (114) of the patient (100) in the PHH repository (110). Thus, the PHH interface (112) includes functionality to secure the PHH account (114). In order to authenticate the user, the PHH interface (112) may have or be connected to an access account (not shown) for each user.

An access account may include authentication information, user preferences, administrative information (e.g., billing information, address information, etc.), an identifier of the user as a healthcare provider or a patient (100), and authorization information for the user. The authentication information may include information necessary to confirm the identity of a user in accordance with one or more embodiments of the invention. For example, the authentication information may include a username and password, data from a security device, biometric data, etc.

The authorization information may specify the data that the user may access. For example, if the user is only a patient (100), then the user may only access their PHH account. In an alternative example, if the user is a healthcare provider (102), then the user may access multiple PHH accounts.

Continuing with FIG. 1, the PHH interface (112) may provide a separate interface for the patient (100) from the healthcare provider (102). Specifically, the PHH interface (112) for the patient allows the patient (100) to access their PHH account and grant or deny access to healthcare providers. In one or more embodiments of the invention, a patient (100) may allow all or only a portion of healthcare providers' access to the patient's PHH account. Specifically, the patient (100) may grant access to only healthcare providers who have an existing relationship with the patient (100). By granting access to healthcare providers who have an existing relationship, the patient (100) may check-in with the healthcare provider (102) whom the patient (100) have intermittent office visits using their biometric identification data in one or more embodiments of the invention.

Alternatively, the patient (100) may provide access to all healthcare providers. By granting access to all healthcare providers, the patient (100) may receive healthcare from the healthcare provider (102) regardless of whether the patient (100) is incapacitated, such as by being unconscious, incognizant, or unable to communicate. For example, when an unconscious patient, who has granted all healthcare providers access, is admitted to an emergency room, the emergency room may obtain the PHH of the unconscious patient from the PHH account of the unconscious patient. In one or more embodiments of the invention, when a patient (100) grants access to all healthcare providers, only healthcare providers who have an access account may access the PHH account of the patient (100).

Continuing with the PHH interface (112), a patient (100) may view and update the patient's PHH through the submission of healthcare data and biometric identification data (126). In one or more embodiments of the invention, the PHH interface (112) may allow the patient (100) to interact with the patient's PHH by categories of healthcare data in the PHH. For example, the categories may be based on the age of the patient (100) at the time in which the PHH entry is created (e.g., child, 20-29 years old, etc.), bodily system affected (e.g., skeletal, digestive, nervous, etc.), healthcare provider (102) treating patient (102), specialty of a physician, or any other grouping of healthcare data in the PHH.

In contrast to the PHH interface (112) for the patient (100), the PHH interface (112) for the healthcare provider (102) enables a healthcare provider (102) to access PHH accounts for multiple patients in the PHH repository (110). In one or more embodiments of the invention, the PHH interface (112) for the healthcare provider (102) includes a mechanism for a healthcare provider (102) to submit biometric identification information (126) and receive the common identifier (128) for the patient (100). The PHH repository (108) may also allow the healthcare provider (102) to obtain healthcare data in the PHH account (114). The PHH interface for the healthcare provider may further allow the healthcare provider (102) to update the patient's PHH account (114).

Figure 2:
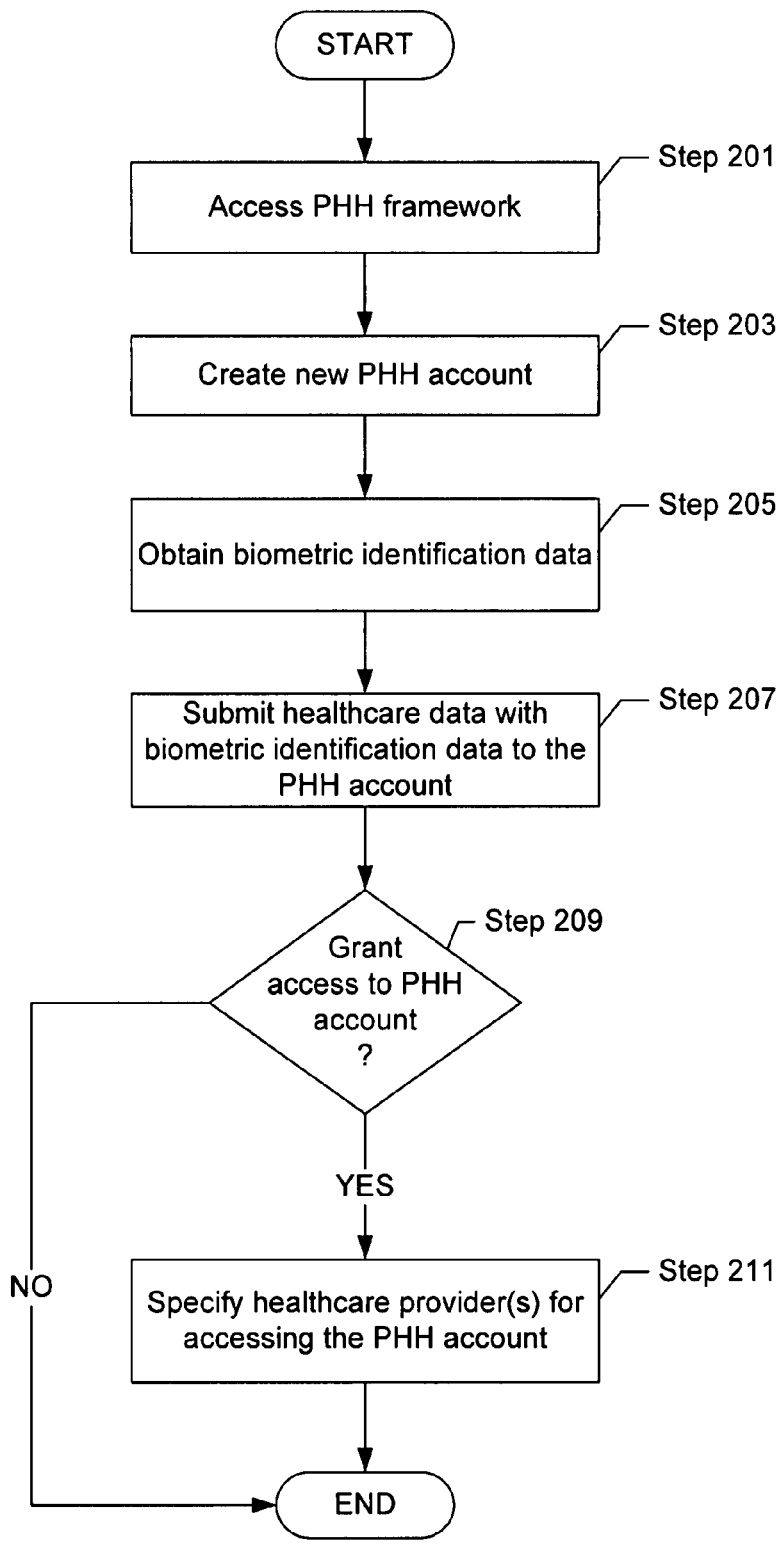
FIGS. 2-4 show flowcharts of a method in accordance with one or more embodiments of the invention.
Figure 3:
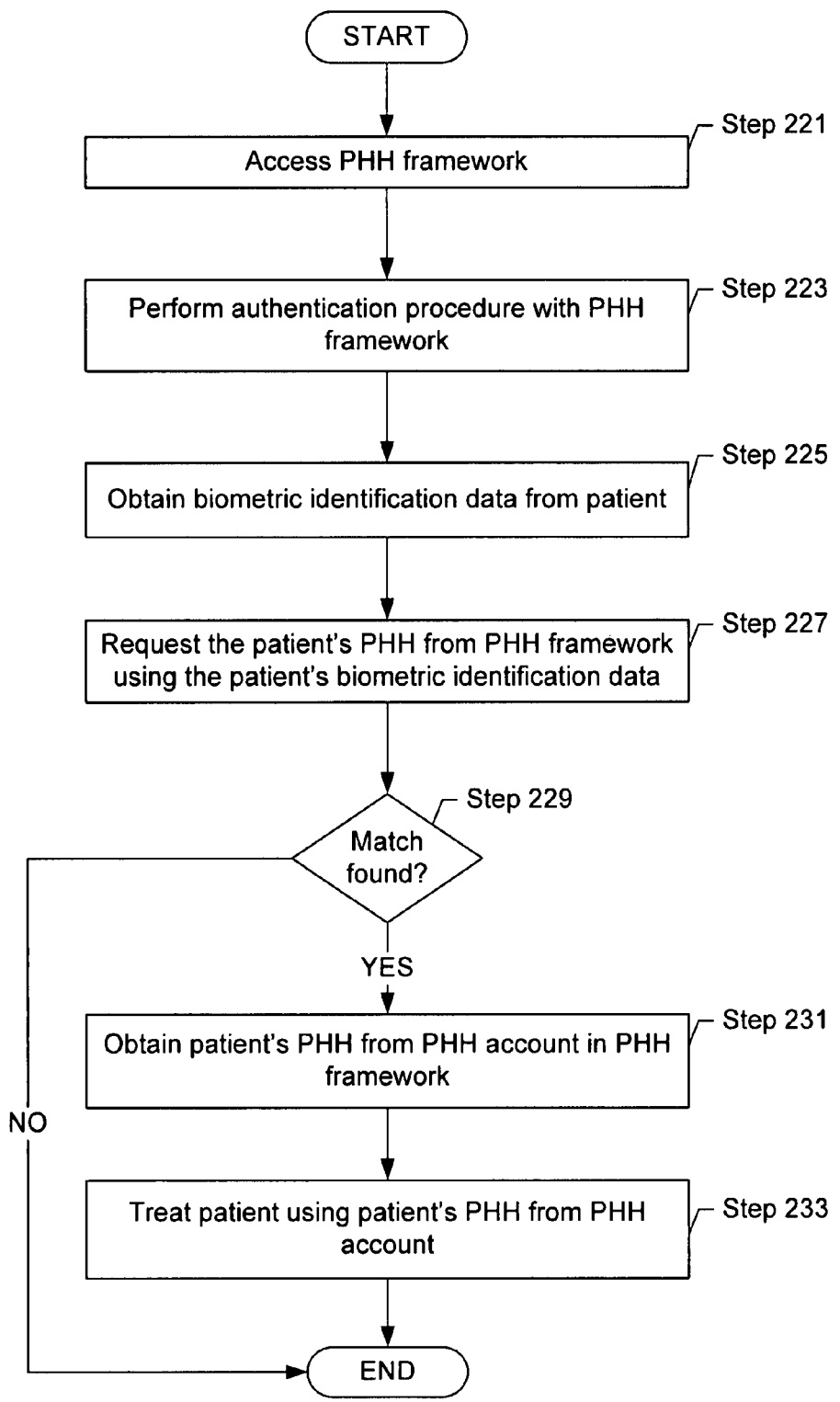
Figure 4:
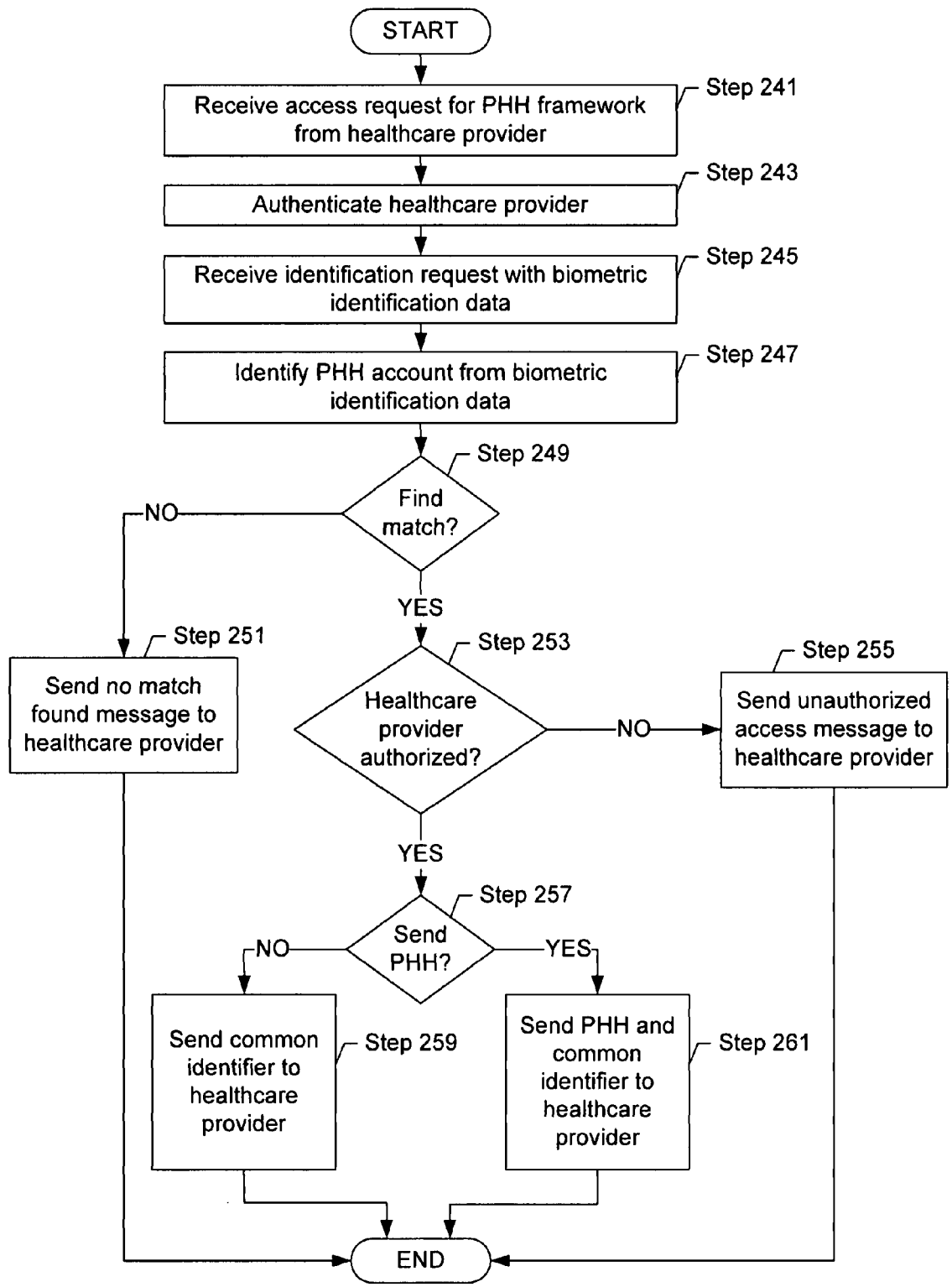

FIGS. 2-4 show flowcharts of a method in accordance with one or more embodiments of the invention. While the various steps in these flowcharts are presented and described sequentially, one of ordinary skill will appreciate that some or all of the steps may be executed in different orders and some or all of the steps may be executed in parallel.

FIG. 2 shows a flowchart of a method for the creation and population of a PHH account in accordance with one or more embodiments of the invention. Initially, the PHH framework is accessed (201). The patient may access the PHH framework by entering a uniform resource identifier of the PHH framework in a web browser, by opening a client-side application stored locally on the user's device, or performing any other operation for accessing a remote system.

Alternatively, a healthcare provider may access the PHH framework on behalf of the patient. For example, before a first office visit with the healthcare provider, the healthcare provider may create the PHH account for the patient. In the example, the patient may provide the healthcare provider with biological matter (e.g., blood sample) or a print from which biometric identification data may be obtained to populate in the PHH account. The healthcare provider may access the PHH framework in a manner similar to the patient accessing the PHH framework. Further, the healthcare provider that creates the PHH account may be different from the healthcare provider that accesses the account to obtain the patient's PHH.

Continuing with FIG. 2, a new PHH account is created (Step 203). In order to create a new PHH account, a link in a web browser may be enabled or data requesting the creation may be submitted in an online form. The creation of the new PHH account may also cause the creation of an access account. For example, when the patient creates the PHH account, the patient submits new authentication information for the PHH interface to confirm the identity of the patient in subsequent accesses to the PHH account. Thus, the new authentication information may be used to create an access account for the patient. In another example, if a healthcare provider is creating an account for the patient, then the account may generate an identifier and temporary password which the healthcare provider may give to the patient.

Further, biometric identification data is obtained (Step 205). In one or more embodiments of the invention, a biometric scanner is used to obtain the biometric identification data. The patient may provide biological matter or a print to be scanned by the biometric scanner. The biometric scanner obtains biometric identification data from the print or the biological matter using a variety of techniques known in the art. For example, if the biometric scanner is a fingerprint reader, then the fingerprint reader may scan the finger and create a computer readable image of the ridges and valleys in the fingerprint.

Alternatively, the patient may send the biological matter to a third party. The third party may use a biometric scanner to obtain biometric identification data from the biological matter. The third party may submit the biometric identification data to the PHH account of the patient or may send the biometric identification data to the patient to submit.

The biometric identification data and the healthcare data may be submitted to the PHH account (Step 207). The PHH interface may include a mechanism for a user (i.e., patient or healthcare provider) to directly submit healthcare data in the PHH account or authorize obtaining the healthcare data to populate PHH account from third parties.

For example, the PHH interface may include a computer generated form with fields in which the healthcare data may be entered. Alternatively, the PHH interface may dynamically lead the user through a questionnaire to answer and populate the PHH account using the answers. For example, a question may be displayed asking whether the user has had any surgeries with radio buttons from which the user may select "yes" or "no". If the user selects "yes", then a question may be displayed which requests that the user enter specific information about the surgery, such as type, date, surgeon, etc.

Further, the PHH interface may also or alternatively request information to authorize the PHH engine to populate the PHH account directly from medical records. For example, the patient may submit information granting permission to the PHH engine to obtain the PHH directly from the healthcare providers that are currently or have in the past treated the patient.

The biometric identification data may be submitted to the PHH account directly from the biometric scanner or by uploading a file stored locally. For example, the biometric identification scanner may be designed so as to store the biometric identification data directly into the PHH account. Alternatively, an application on a user's computer may be used to operate the biometric scanner and store the biometric identification data in a location specified by the user. If the location is local on the user's computer, then the PHH interface may allow a user to specify the location and upload the biometric identification data into the PHH account of the patient.

In addition to submitting healthcare data with the biometric identification data, a determination is made whether to grant access to the PHH account (Step 209). Typically, the determination is made by the patient when deciding which healthcare providers should have access to the PHH account. Alternatively, a default value may be used which grants access to only the patient.

If a determination is made to grant access to the PHH account, then the patient specifies one or more healthcare providers for accessing the PHH account (Step 211). Specifically, the patient may determine whether only healthcare providers who have an existing relationship with the patient are able to access the PHH account, or whether the PHH account is accessible for all healthcare providers.

For each healthcare provider or group of healthcare providers, the patient may also specify the portion of the healthcare data that is accessible and which healthcare data is the healthcare provider unauthorized to access. The patient may also specify whether the healthcare provider has both view and modify privileges. The patient may specify portions of the PHH account according to categories of the healthcare data or according to specific entries in the healthcare data. For example, the patient may grant all healthcare providers access to healthcare data that would be required in an emergency situation, such as history of major illness and blood type while denying access to optional healthcare data such as infertility treatments. In the example, the patient may also specify that a specific healthcare provider that has a history of treating the patient may view all healthcare data.

Various different methods may be performed to allow a patient to grant and deny access to portions of the PHH account. The following is only a few of the different mechanisms which may be used.

One method may involve the patient selecting specific entries in the healthcare data. For example, the patient may select checkboxes that are related to specific medications, surgeries, treatments, or conditions. In the example, the patient may specify using the checkboxes whether the healthcare provider(s) has both read and write access.

In another method, the patient may select categories of healthcare data in the PHH account. For example, the patient may select all medications, all surgeries, all lab results, or all entries generated for a particular healthcare provider or medical condition. The selection may be performed using checkboxes as described above or by using one or more links.

Alternatively, the patient may grant access by explicitly denying access to portions of the healthcare data. Specifically, the patient may specify that the healthcare provider(s) may access the entire healthcare account except for the portion specified by the patient. The patient may make the specification by selecting categories or checkboxes as described above.

In another method, the healthcare provider(s) may request access to specific portions of the healthcare data. The request may be transmitted to the patient using email or other methods of notification. In response to the request, the patient may specify whether the healthcare provider(s) may access the account. For example, patient may grant a podiatrist privilege to request data from the account. In response, the podiatrist, or a podiatry assistant, may select different portions of the PHH account that would affect how the podiatrist manages the patient's healthcare. For example, the assistant may select medications, surgeries, and history of chronic illnesses without selecting urology related lab results. An email containing the selections may be transmitted to the patient. The email may request that the patient respond with granting access or denying access to the requested healthcare information. The patient may respond via email or using the PHH account.

The above examples are intended as only a few of the different mechanisms that may be used to grant access to healthcare data. One skilled in the art will appreciate that any number of equivalent methods may be performed.

Once the PHH account is created and populated, healthcare providers whom have been granted access may use the PHH account of the patient. Typically, each healthcare provider that accesses the PHH account of the patient has an access account. The access account allows the healthcare provider to authenticate themselves and secure the patient's PHH. The healthcare provider may create the access account by providing authentication data, administrative information, billing information, and other such information. Using the access account, the healthcare provider may access the information in the PHH account of the patient.

FIG. 3 shows a flowchart of a method for a healthcare provider to use the patient's PHH account in accordance with one or more embodiments of the invention. Initially, the healthcare provider accesses the PHH framework (Step 221). The healthcare provider may access the PHH framework in the same manner as described above in Step 201 of FIG. 2. Next, the healthcare provider performs an authentication procedure (Step 223). Specifically, the healthcare framework attempts to confirm the identity the healthcare provider. Thus, the authentication procedure may involve the healthcare provider entering a username, password, pin number, biometric data (e.g., a fingerprint), or any other procedure.

Once the healthcare provider is authenticated, biometric identification data is obtained from the patient (Step 225). Obtaining the biometric data may be performed using, for example, the biometric scanner as described above in step 205 of FIG. 2. At this stage, the patient permits the healthcare provider to obtain the biometric identification data. Permitting a healthcare provider to obtain the biometric identification data may be performed directly or indirectly. For example, the patient may place a finger on a fingerprint scanner which is operated by the healthcare provider. In another example, if the patient is incapacitated, then the patient permits the healthcare provider to obtain the biometric identification data by having a PHH account with biometric identification data and granting the healthcare provider access to the healthcare data in the PHH account.

Using the biometric identification data, the healthcare provider requests the patient's PHH from the PHH framework (Step 227). Specifically, the healthcare provider sends the biometric identification data of the patient to the PHH framework. The biometric identification data may be sent to the PHH framework directly from the biometric scanner or by uploading a file stored locally. For example, the biometric scanner may be designed so as to automatically submit the biometric identification data directly to the PHH account with a request for the PHH of the patient corresponding to the biometric identification data. Alternatively, an application on the healthcare provider's computer may be used to operate the biometric scanner and store the biometric identification data in a location specified by the healthcare provider. If the location is local on the healthcare provider's computer, then the PHH interface may allow a user to specify the location and upload the biometric identification data into the PHH account of the patient.

While not shown in FIG. 3, rather than requesting the patient's PHH, the healthcare provider may request only the common identifier of the patient. For example, in an emergency in which the identity of the patient is unknown, the healthcare provider may access the PHH framework and use the biometric identification data to determine the identity of the patient.

Next, a determination is made whether a match is found (Step 229). Specifically, the PHH framework may respond to the request with an error message indicating that the sending of the request was faulty or the biometric identification data is unusable, a message indicating that a match could not be found, a message indicating that the healthcare provider is unauthorized to access the PHH account of the patient, or a message with the healthcare data or method for accessing the healthcare data.

If a match is not found, or if an error message is returned, then the healthcare provider may treat the patient without using the PHH account of the patient. Alternatively, if the healthcare provider is unauthorized to access the PHH account of the patient, then the healthcare provider may request authorization from the patient or a person/entity that is authorized to act on behalf of the patient.

However, if a match is found, then the patient's PHH is obtained from the PHH account in the PHH framework (Step 231). Thus, the healthcare provider may interact with the PHH account of the patient. Specifically, the healthcare provider may read and write to the portion of the PHH account for which the healthcare provider is authorized to access. Interacting with the PHH may involve the healthcare provider viewing different categories of healthcare data or a particular entry of healthcare data in the PHH account by clicking on a link, selecting a button, or submitting a command in the PHH interface. In response, the PHH interface may request the category or entry of healthcare data from the PHH repository and return the result to the healthcare provider.

Accordingly, the healthcare provider treats the patient using the patient's PHH from the PHH account (Step 233). For example, the healthcare provider may make a diagnosis as to the patient's condition, prescribe certain medications, or otherwise provide healthcare to the patient. When or after treating the patient, the healthcare provider may update the patient's PHH in the PHH account (not shown). For example, the healthcare provider may submit medical notes specifying the treatment plan, new medications, information about the diagnosis, etc.

FIG. 4 shows a flowchart of the PHH framework to interact with a healthcare provider in accordance with one or more embodiments of the invention. Initially, the PHH framework receives an access request from a healthcare provider (Step 241). The PHH framework may determine how to communicate with the healthcare provider based on the access request. For example, the PHH framework may communicate with the healthcare provider via SMS, a website, and/or other communication media.

Next, the PHH engine authenticates the healthcare provider (Step 243). Specifically, after obtaining identifying information of the healthcare provider (e.g., username, internet protocol (IP) address, etc.), the PHH engine may access the authentication and authorization account to find the access account for the healthcare provider. Next, the PHH engine may verify the identity of the healthcare provider using the access account of the healthcare provider.

Next, the PHH framework receives an identification request from the healthcare provider with the biometric identification data (Step 279). The request may be received by receiving the biometric identification data. When the biometric identification data is received, the PHH account is identified from the biometric identification data. Specifically, the biometric identification data that is received is compared with the biometric identification data of each account in the PHH repository. If the PHH repository has an index of the biometric identification data, then the index may be searched for the PHH account.

Next, a determination is made whether a match exists (Step 249). Specifically, a determination is made whether the biometric identification data that is received matches the biometric identification data in a PHH account. A margin of error in the biometric identification data may be accounted for when performing the comparison to determine whether a match is found. If a match is not found, then a "no match found" message is sent to the healthcare provider (Step 251). The "no match found" message may also include an error message about why a match was not found. For example, the error message may specify that the wrong type of biometric identification data (e.g., fingerprint instead of DNA) was sent to the PHH framework.

Alternatively, if a match is found, then a determination is made whether the healthcare provider is authorized to access the PHH account (Step 253). Determining whether the healthcare provider is authorized may be performed by sending a query to the PHH repository requesting whether the PHH account includes authorization for all healthcare providers to access the PHH account or whether the specific healthcare provider sending the request is authorized to access the PHH account. The PHH repository may respond to the request with the data or with an "unauthorized access" message.

Accordingly, if the healthcare provider is not authorized to access the PHH account of the patient, then an "unauthorized access" message is sent to the healthcare provider (Step 255). Alternatively, if the healthcare provider is authorized to access the PHH account, then a determination is made whether to send the PHH of the patient or just the common identifier (Step 257). Determining whether to send the PHH with the common identifier may be based on the type of request, such as whether the healthcare provider is requesting the PHH, and whether the healthcare provider is authorized to receive the PHH with the common identifier. If the PHH is not to be sent to the healthcare provider, then the common identifier is obtained from the PHH repository and sent to the healthcare provider (Step 259).

Alternatively, if the PHH is to be sent to the healthcare provider, then the common identifier and the PHH are sent to the healthcare provider (Step 261). Specifically, in one or more embodiments of the invention, the PHH framework may send the PHH to the healthcare provider in portions as the healthcare provider interacts with the PHH. For example, the PHH framework may process requests for specific portions of healthcare data from the healthcare provider.

In order to process a request, a query may be sent to the PHH repository for healthcare data that is in the PHH account of the patient. The PHH repository may respond to the query with the healthcare data. After determining that the healthcare provider is authorized to view the healthcare data, the PHH interface forwards the healthcare data to the healthcare provider.

In the following example, consider the scenario in which a patient, living in Boston, Mass., is a diabetic. In the process of visiting the physician, the patient creates a PHH account. The PHH account includes a medical history of the patient's diabetes and treatment with insulin dosage amounts. During a first visit with the physician, the patient uses a fingerprint scanner to send fingerprint data to the PHH account. Thus, during subsequent visits, the patient checks-in to the physician's office by using the fingerprint scanner at the physician's office. An assistant of the physician sends the fingerprint to the PHH framework in order to obtain a copy of the patients PHH for each visit. Further, the patient accesses the PHH framework at home to review the changes in the patient's health as recorded in healthcare data in the PHH account. While reviewing the PHH account, the patient decides to grant access to all healthcare providers for emergency situations.

In the example, consider the scenario in which the patient decides to go hiking in mountains near Anchorage, Ak. While hiking, the patient slips on ice and loses consciousness. Nearby hikers call emergency personnel and the unconscious patient is airlifted from the mountains to the nearest hospital. During the helicopter ride, the emergency medical technician (EMT) uses a fingerprint scanner to create a scanned image of the patient's finger. Using a portable device with networking capabilities, the EMT sends the image to the PHH framework.

Using the image, the PHH framework identifies the PHH account of the patient and determines that all healthcare providers are authorized to access the PHH account. Accordingly, the PHH framework sends the patient's PHH to the portable device of the EMT. Thus, upon noticing that the patient is a diabetic and seeing the insulin dosage amounts, the EMT ensures that other medical personnel treating the patient are aware and that the diabetes is monitored and insulin is given.

Figure 5:
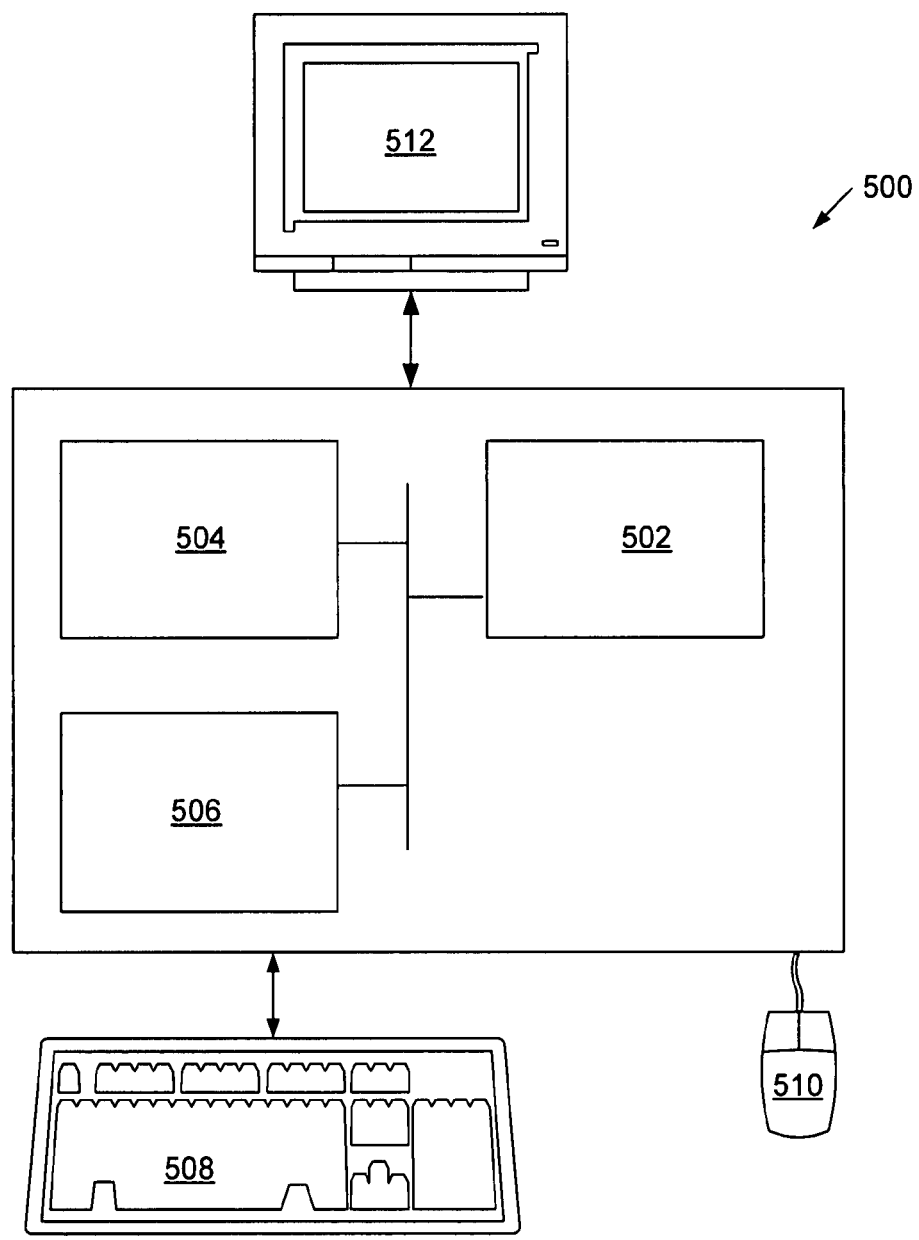
FIG. 5 shows a computer system in accordance with one or more embodiments of the invention.

Embodiments of the invention may be implemented on virtually any type of computer regardless of the platform being used. For example, as shown in FIG. 5, a computer system (500) includes a processor (502), associated memory (504), a storage device (506), and numerous other elements and functionalities typical of today's computers (not shown). The computer (500) may also include input means, such as a keyboard (508) and a mouse (510), and output means, such as a monitor (512). The computer system (500) is connected to a local area network (LAN) or a wide area network (e.g., the Internet) (not shown) via a network interface connection (not shown). Those skilled in the art will appreciate that these input and output means may take other forms.

Further, those skilled in the art will appreciate that one or more elements of the aforementioned computer system (500) may be located at a remote location and connected to the other elements over a network. Further, the invention may be implemented on a distributed system having a plurality of nodes, where each portion of the invention (e.g., PHH interface, administrative information, biometric identification data, etc.) may be located on a different node within the distributed system. In one embodiment of the invention, the node corresponds to a computer system. Alternatively, the node may correspond to a processor with associated physical memory. The node may alternatively correspond to a processor with shared memory and/or resources. Further, software instructions to perform embodiments of the invention may be stored on a computer readable medium such as a compact disc (CD), a diskette, a tape, a file, or any other computer readable storage device.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for obtaining healthcare comprising:
   obtaining, by a healthcare provider, biometric identification data from a non-communicative patient;
   generating, by the healthcare provider using a computer processor, an identification request comprising the biometric identification data;
   sending, via a computer network, the identification request to a Personal Health History (PHH) framework comprising a PHH account for the non-communicative patient, wherein the PHH framework selects the PHH account identified by the biometric identification data from a plurality of PHH accounts, and wherein the PHH account for the non-communicative patient comprises a common identifier;
   receiving, by the healthcare provider, the common identifier associated with the PHH account from the PHH framework;
   identifying the non-communicative patient by the healthcare provider using the common identifier; and
   administering a treatment for a health condition of the non-communicative patient by the healthcare provider.

2. The method of claim 1, further comprising:
   submitting, by the healthcare provider, healthcare data for the non-communicative patient to the PHH account.

3. The method of claim 2, wherein the healthcare data comprises data associated with at least one selected from a group consisting of a medication, a diagnosis, the treatment, and a medical note.

4. The method of claim 1, further comprising:
   updating, by the healthcare provider, the PHH for the non-communicative patient based on the treatment received.

5. The method of claim 1, wherein the biometric identification data is data derived from a group consisting of a scan of a print and a retinal scan.

6. The method of claim 1, wherein the biometric identification data is data defining a deoxyribonucleic acid (DNA) sequence.

7. The method of claim 1, wherein the non-communicative patient is in an emergency room.

8. The method of claim 1, wherein the PHH framework verifies that the healthcare provider has permission to access the PHH account, wherein the healthcare provider is one of the plurality of healthcare providers.

9. A method for patient identification comprising:
   receiving, via a computer network by a Personal Health History (PHH) framework executing on a computer processor, an identification request from a healthcare provider, wherein the identification request comprises biometric identification data for a non-communicative patient;
   selecting, by the PHH framework, a PHH account identified by the biometric identification data from a plurality of PHH accounts, wherein the PHH account for the non-communicative patient comprises a common identifier;
   obtaining, by the PHH framework, the common identifier from the PHH account; and
   sending via the computer network by the PHH framework the common identifier to the healthcare provider, wherein the non-communicative patient receives treatment for a medical condition by the healthcare provider using the common identifier.

10. The method of claim 9, further comprising:
    receiving, by the PHH framework, healthcare data for the non-communicative patient; and
    populating the PHH account of the non-communicative patient according to the received healthcare data, wherein the healthcare data is sent with the common identifier.

11. The method of claim 10, wherein the healthcare data comprises data associated with at least one selected from a group consisting of a medication, a diagnosis, the treatment, and a medical note.

12. The method of claim 9, wherein the biometric identification data is derived from at least one selected from a group consisting of a scan of a print, a retinal scan, and a DNA sequence.

13. The method of claim 9, wherein the non-communicative patient is located in an emergency room.

14. The method of claim 9, further comprising:
    creating an access account allowing each of a plurality of healthcare providers access to a PHH framework; and
    granting the plurality of healthcare providers access to the PHH account using the access account, wherein the healthcare provider is one of the plurality of healthcare providers.

15. A system for patient identification comprising:
    a PHH framework, executing on a computer processor, comprising:
       a plurality of PHH accounts, wherein each of the PHH accounts comprises a common identifier for a corresponding patient of a plurality of patients; and
       a PHH interface configured to:
          receive, via a computer network, an identification request from a healthcare provider, wherein the identification request comprises first biometric identification data for a non-communicative patient of the plurality of patients, wherein the first biometric identification data is obtained by the healthcare provider using a biometric scanner;
          access a first PHH account of the plurality of PHH accounts identified by the first biometric identification data received from the healthcare provider;
          obtain the common identifier for the non-communicative patient from the first PHH account; and
          send, via the computer network, the common identifier to the healthcare provider, wherein the non-communicative patient receives treatment for a medical condition by the healthcare provider using the common identifier.

16. The system of claim 15, wherein the PHH interface is further configured to:
    receive second biometric identification data from a biometric scanner used by a communicative patient of the plurality of patients; and
    populate, with healthcare data and the second biometric identification data of the communicative patient, the PHH account of the plurality of PHH accounts.

17. The system of claim 16, wherein the healthcare data comprises data associated with at least one selected from a group consisting of a medication, a diagnosis, the treatment, and a medical note.

18. The system of claim 15, wherein the first biometric identification data is derived from one selected from a group consisting of a scan of a print, a retinal scan, and a DNA sequence.

19. The system of claim 15, wherein the non-communicative patient is located in an emergency room.

20. A computer readable medium comprising computer readable program code embodied therein for causing a computer system to:
- receive, via a computer network by a Personal Health History (PHH) framework, an identification request from a healthcare provider, wherein the identification request comprises biometric identification data for a non-communicative patient;
- select, by the PHH framework, a PHH account identified by the biometric identification data from a plurality of PHH accounts, wherein the PHH account for the non-communicative patient comprises a common identifier;
- obtain, by the PHH framework, the common identifier from the PHH account; and
- send, via the computer network by the PHH framework, the common identifier to the healthcare provider, wherein the non-communicative patient receives treatment for a medical condition by the healthcare provider using the common identifier.

21. The computer readable medium of claim 20, wherein the computer readable program code further causes the computer to:
- receive, by the PHH framework, healthcare data for the non-communicative patient; and
- populate the PHH account of the non-communicative patient according to the received healthcare data, wherein the healthcare data is sent with the common identifier.

22. The computer readable medium of claim 21, wherein the healthcare data comprises data associated with at least one selected from a group consisting of a medication, a diagnosis, a treatment, and a medical note.

23. The computer readable medium of claim 20, wherein the biometric identification data is derived from one selected from a group consisting of a scan of a print, a retinal scan, and a DNA sequence.

24. The computer readable medium of claim 20, wherein the non-communicative patient is located in an emergency room.

25. A computer readable medium comprising computer readable program code embodied therein for causing a computer system to:
- obtain biometric identification data from a non-communicative patient;
- generate an identification request comprising the biometric identification data;
- send, via a computer network, the identification request to a Personal Health History (PHH) framework comprising a PHH account for non-communicative patient, wherein the PHH framework selects the PHH account identified by the biometric identification data from a plurality of PHH accounts comprising the PHH framework, and wherein the PHH account for the non-communicative patient comprises a common identifier;
- receive the common identifier associated with the PHH account the PHH framework; and
- identify the non-communicative patient using the common identifier, wherein the non-communicative patient receives a treatment for a health condition administered by a healthcare provider using the common identifier.

26. The computer readable medium of claim 25, wherein the computer readable program code further causes the computer to:
- submit healthcare data for the non-communicative patient to the PHH account.

27. The computer readable medium of claim 26, wherein the healthcare data comprises data associated with at least one selected from a group consisting of a medication, a diagnosis, the treatment, and a medical note.

28. The computer readable medium of claim 25, wherein the computer readable program code further causes the computer to:
- update the PHH for the non-communicative patient based on the treatment received.

29. The computer readable medium of claim 25, wherein the biometric identification data is data derived from a group consisting of a scan of a print and a retinal scan.

30. The computer readable medium of claim 25, wherein the biometric identification data is data defining a deoxyribonucleic acid (DNA) sequence.

31. The computer readable medium of claim 25, wherein the non-communicative patient is in an emergency room.

32. The computer readable medium of claim 25, wherein the PHH framework verifies that the healthcare provider has permission to access the PHH account, wherein the healthcare provider is one of the plurality of healthcare providers.

* * * * *